(12) United States Patent
Ness et al.

(10) Patent No.: US 7,799,752 B2
(45) Date of Patent: Sep. 21, 2010

(54) COMPOSITIONS COMPRISING ENCAPSULATED MATERIAL

(75) Inventors: Jeremy Nicholas Ness, Ashford (GB); John McNamee, Castle Hill (AU)

(73) Assignee: Quest International Services B.V., Naarden (NL)

( * ) Notice: Subject to any disclaimer, the term of this patent is extended or adjusted under 35 U.S.C. 154(b) by 820 days.

(21) Appl. No.: 10/524,415

(22) PCT Filed: Aug. 12, 2003

(86) PCT No.: PCT/GB03/03518

§ 371 (c)(1),
(2), (4) Date: Feb. 14, 2005

(87) PCT Pub. No.: WO2004/016234

PCT Pub. Date: Feb. 26, 2004

(65) Prior Publication Data

US 2006/0039934 A1    Feb. 23, 2006

(30) Foreign Application Priority Data

Aug. 14, 2002  (EP) ................... 02255677
Oct. 25, 2002  (EP) ................... 02257436

(51) Int. Cl.
*A61K 7/46* (2006.01)
(52) U.S. Cl. ................................................ 512/4
(58) Field of Classification Search ................ 512/4
See application file for complete search history.

(56) References Cited

U.S. PATENT DOCUMENTS 3,959,540 A * 5/1976 Leiberich et al. ........... 428/35.7
4,394,287 A    7/1983 Scarpelli
4,999,189 A    3/1991 Kogan et al.
5,059,416 A   10/1991 Cherukuri et al.
5,500,223 A *  3/1996 Behan et al. .............. 424/451
6,194,375 B1 * 2/2001 Ness et al. .................... 512/4

FOREIGN PATENT DOCUMENTS

| EP | 0 391 556 A1 | 10/1990 |
| EP | 0 453 001 A1 | 10/1991 |
| EP | 0 465 238 A1 | 1/1992 |
| EP | 1118382 A1 | 7/2001 |
| EP | 1247568 A1 | 10/2002 |
| FR | 1534285 | 7/1968 |
| FR | 2 698 561 | 6/1994 |
| WO | WO 92/20771 | 11/1992 |
| WO | WO 96/03041 | 2/1996 |
| WO | WO 01/51196 | 7/2001 |
| WO | WO 02/074430 A1 | 11/2002 |

OTHER PUBLICATIONS

Natske et al., Spherical Microparticles having an inner wax coating deposited around biologically active compounds, Feb. 8, 1996, International Application Published Under the PCT, WO 96/03041.*
Ness, Perfume Encapsulates, Sep. 26, 2002, International Application Published Under the PCT, WO 02/074430.*

* cited by examiner

*Primary Examiner*—Johann R Richter
*Assistant Examiner*—Ali Soroush
(74) *Attorney, Agent, or Firm*—Morgan Lewis & Bockius LLP

(57) ABSTRACT

A composition such as a water-based consumer product comprises material (e.g. perfume) encapsulated within shell capsules, each capsule comprising an encapsulating wall having an inner surface and an outer surface, with a coating on the inner surface and/or outer surface of the shell wall, the composition further comprising surfactant and/or solvent. The coating can improve the barrier properties of the shell and can enhance retention of the encapsulated materials within the shell.

34 Claims, 1 Drawing Sheet

Figure 1 – Transmission Light Micrographs of Shampoos BR2 and B4 after one month's storage at 37°C (field width ~160μm)
Shampoo BR2
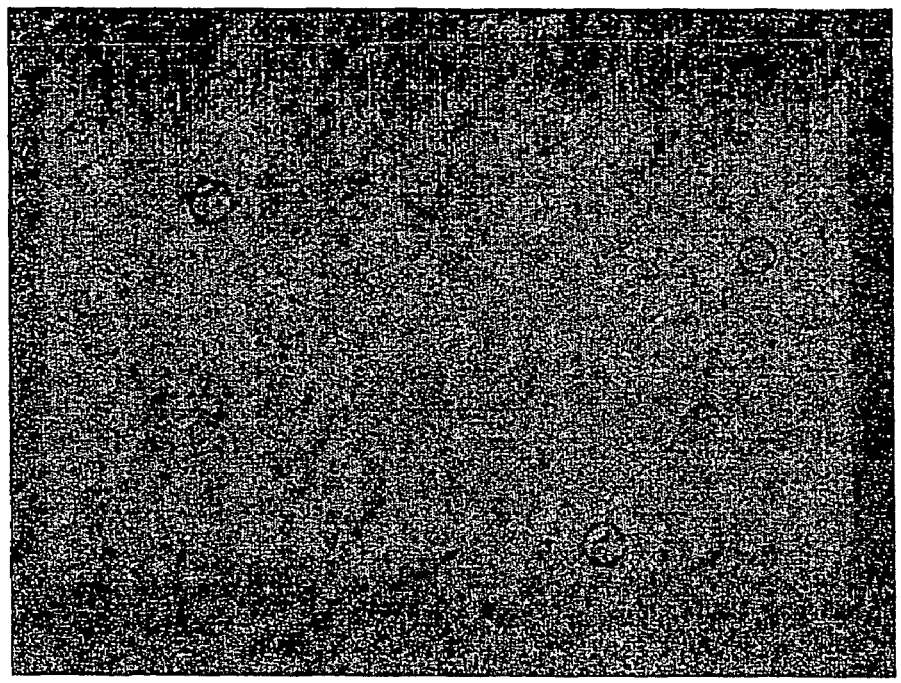
Shampoo B4
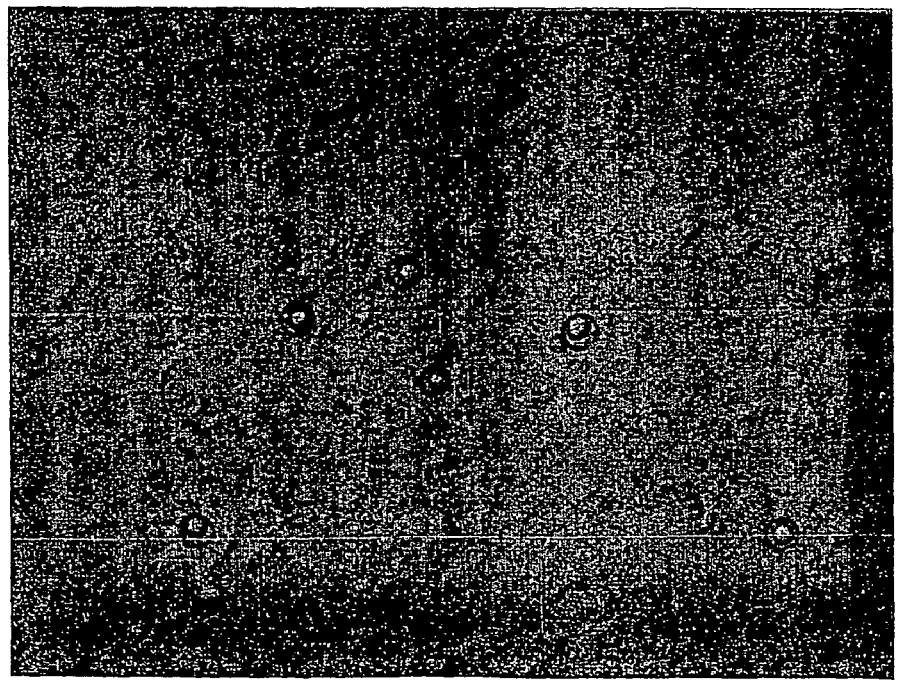

COMPOSITIONS COMPRISING ENCAPSULATED MATERIAL

FIELD OF THE INVENTION

This invention concerns compositions, particularly consumer products, containing encapsulated material, and relates to such compositions and encapsulates.

BACKGROUND TO THE INVENTION

It is known to encapsulate perfume or other materials, in small capsules (or microcapsules), typically having a diameter less than 1000 microns, for a variety of reasons relating to the protection, delivery and release of the perfume or other material. One type of capsule, referred to as a wall or shell capsule, comprises a generally spherical hollow shell of e.g. perfume-insoluble material, typically polymer material, within which perfume or other material is contained.

If such capsules are incorporated in certain solvent and/or surfactant-containing consumer products, e.g. shampoos, stability problems can arise, with the encapsulated material tending to leach out of the capsules into the product over time, at least in cases where the capsule contents are soluble in ingredients of the product.

The present invention aims to address such stability problems.

SUMMARY OF THE INVENTION

In one aspect the present invention provides a composition comprising material encapsulated within shell capsules, each capsule comprising an encapsulating wall having an inner surface and an outer surface, with a coating on the inner surface and/or outer surface of the shell wall; and surfactant and/or solvent.

The composition may be a fragranced composition. The term "fragranced composition" is used to mean a composition containing at least 0.1% by weight of one or more perfume materials (as discussed below). The perfume material may be present in the composition, encapsulated within shell capsules and/or in unencapsulated form.

Preferably, the composition is a product, particularly a consumer product, conveniently in liquid or solid form. Preferably, the product is a liquid product and more preferably a water-based product.

Examples of products include fabric care products such as fabric detergents e.g. laundry liquids and laundry powders, fabric conditioners e.g. rinse conditioners and sheet conditioners, fabric treatment products including fabric refresher products, e.g. sprays, starch sprays, ironing sprays and stain remover sprays; personal care products such as skin care, hair care and personal cleansing products including hair shampoos, body washes and shower gels, bath foams, toilet soap, toothpaste, mouthwash, deodorants and antiperspirants, skin creams and lotions and the like, colognes, body sprays, personal perfumes; and household products such as toilet cleaners, hard surface cleaners, abrasive cleaners, general purpose cleaners and bleaches.

Typically the product will be of generally conventional composition, as is known to those skilled in the art, and may comprise further excipients appropriate to the nature of the product. Suitable excipients may include fixatives, softening agents, enzymes, builders, bleaching agents, bleach activators, suspending agents, thickeners, silicones, emollients, humectants, vitamins, flavours, perfumes, antibacterial agents, etc. Details of suitable excipients for products such as fabric detergents, fabric conditioners, personal cleansing products, particularly hair shampoos and shower gels, and household cleaners are described in WO 98/28396 and WO 98/28398. Details of suitable excipients for 'leave-on' products such as deodorants and antiperspirants, skin creams, colognes etc, are described, for example, in L. Appell, "The Formulation and Preparation of Cosmetics Fragrances and Flavours", Micelle Press (1994), Chapter 1.

The encapsulated material generally comprises a first material which is conveniently at least partially, preferably substantially and more preferably completely soluble, in the surfactant and/or solvent of the compositions defined herein. Preferably, the first material is substantially water-insoluble to facilitate preparation of an emulsion or dispersion of the material prior to encapsulation.

Suitable types of such first materials which may be encapsulated within shell capsules as defined herein include perfumes, cosmetic ingredients such as moisturisers, conditioning agents, sunscreening agents, physiological coolants and emollient oils, agrichemicals such as insecticides and herbicides, dental flavours, insect repellents, antimicrobial agents, deodorant actives, or mixtures thereof.

As is well known, a perfume normally consists of a mixture of a number of perfume materials, each of which has an odour or fragrance. The number of perfume materials in a perfume is typically 10 or more. The range of fragrant materials used in perfumery is very wide; the materials come from a variety of chemical classes, but in general are water-insoluble oils. In many instances, the molecular weight of a perfume material is in excess of 150, but does not exceed 300.

Perfumes used in the present invention can be mixtures of conventional perfume materials. Such materials are, for example, natural products such as extracts, essential oils, absolutes, resinoids, resins, concretes etc., but also synthetic materials such as hydrocarbons, alcohols, aldehydes, ketones, ethers, acids, esters, acetals, ketals, nitriles, etc., including saturated and unsaturated compounds, aliphatic, carbocyclic, and heterocyclic compounds.

Such perfume materials are mentioned, for example, in S. Arctander, Perfume and Flavor Chemicals (Montclair, N. J., 1969), in S. Arctander, Perfume and Flavor Materials of Natural Origin (Elizabeth, N. J., 1960) and in "Flavor and Fragrance Materials—1991", Allured Publishing Co. Wheaton, Ill. USA.

Examples of perfume materials which can be used in the invention are: geraniol, geranyl acetate, linalol, linalyl acetate, tetrahydrolinalol, citronellol, citronellyl acetate, dihydromyrcenol, dihydromyrcenyl acetate, tetrahydromyrcenol, terpineol, terpinyl acetate, nonpol, nopyl acetate, 2-phenyl-ethanol, 2-penylethyl acetate, benzyl alcohol, benzyl acetate, benzyl salicylate, styrallyl acetate, benzyl benzoate, amyl salicylate, dimethylbenzyl-carbinol, trichloromethylphenyl-carbinyl acetate, p-tert-butylcyclohexyl acetate, isononyl acetate, vetiveryl acetate, vetiverol, α-hexylcinnamaldehyde, 2-methyl-3-p-tert-butylpheyl)propanal, 2-methyl-3-(p-isopropylphenyl)propanal, 2-(p-tert-butylpheyl) propanal, 2,4-dimethyl-cyclohex-3-enyl-carboxaldehyde, tricyclodecenyl acetate, tricyclodecenyl propionate,4-(4-hydroxy-4-methylpentyl)-3-cyclohexenecarboxyaldehyde, 4-(4-methyl-3-pentenyl)-3-cyclohexenecarboxaldehyde, 4-acetoxy-3-pentyl-tetrahydropyran, 3-carboxymethyl-2-pentylcyclopentane, 2-n-heptylcyclopentanone, 3-methyl-2-pentyl-2-cyclopentenone, n-decanal, n-dodecanal, 9-decenol-1, phenoxyethyl isobutyrate, phenyl-acetaldehyde dimethyl-acetal, phenylacetaldehyde diethylacetal, geranyl nitrile, citronellyl nitrile, cedryl acetate, 3-isocamphylcyclohexanol, cedryl methyl ether, isolongifolanone, aubepine nitrile, aubepine, heliotropin, coumarin, eugenol, vanillin, diphenyl oxide, hydroxycitronellal, ionones, methylionones, isomethylionones, irones, cis-3-hexenol and esters thereof, indan musks, tetralin musks, isochroman musks, macrocyclic ketones, macrolactone musks, ethylene brassylate.

The perfume should be substantially free of water-miscible materials such as dipropylene glycol. Solvents which can be used for perfumes include, for example: diethyl phthalate, triethyl citrate, etc.

Examples of suitable moisturisers, emollient oils and conditioning agents useful herein include cyclic silicones, esters such as isopropyl myristate, olive oil, mineral oil and tercopheryl actetate. See also WO 96/12468 page 56.

Examples of sunscreening agents useful herein include octyl methoxy cinnamate available for example as Parsol MCX (Parsol MCX is a Trade Mark) from Hoffman LaRoche, nonylmethoxycinnamate, 2-ethyl hexyl salicylate, benzophenone, and para amino benzoic acid and its esters. See also WO 96/12468 page 55 to 56.

Examples of suitable insecticides useful herein include pyrethroid compounds such as pyrethrum and 3-phenoxybenzyl 2,2-dimethyl-3-12',2'-dichlorovinyl)-cyclopropane-carboxylate (permethrin).

A wide range of well known dental flavours may be used which may be natural or synthetic, e.g. oil of spearmint, peppermint, wintergreen, sassafras, clove, sage, eucalyptus, marjoram, cinnamon, lemon and orange, menthol, eugenol, aniseed, cinnamic aldehyde, menthyl acetate and methyl salicylate.

As examples of suitable insect repellents may be mentioned N,N-diethyl-m-toluamide (DEET), benzamide, methyl neodecanamide, hexane-1,2-diol, methyl and 3-(N-butylacetylamino)-propionic acid ethyl ester, commercially available as Merck IR 3535 from Merck & Co. Inc.

Preferably, the antimicrobial agent is water-insoluble. An example of a suitable water-insoluble antimicrobial agent for use herein is 5-chloro-2-[(2,4-dichlorophenyl)oxy]phenol, more commonly known as Triclosan (Triclosan is a Trade Mark), commercially available for example as Irgasan DP300 (Irgasan DP300 is a Trade Mark) from Ciba Speciality Chemicals.

Suitable deodorant actives include, for example, materials such quaternary ammonium compounds e.g. cetyl-trimethylammonium bromide, lauroyl sarcosine, N-myristoyl glycine, diaminoalkyl amides such as L-lysine hexadecyl amide, zinc citrate and zinc pyrithione.

Examples of suitable physiological coolants useful herein include menthol, menthol PCA, menthyl lactate, menthyl succinate and menthyl carbonate.

The encapsulated material may comprise one or more first materials.

In addition to the above-described first material of the shell capsules, or in the alternative, there may also be present one or more second materials which may be insoluble in the surfactant and/or solvent of the compositions defined herein. Examples of such insoluble materials include certain conditioning agents (e.g. high molecular weight dimethicones), pigments (e.g. titanium dioxide) and anti-dandruff agents (e.g. zinc pyrethione).

Optional further materials which may be encapsulated in the shell capsules herein include dyes and preservatives etc.

In a preferred embodiment, the encapsulated material is a perfume composition, which typically comprises at least 80% and preferably at least 90% by weight of the total weight of the perfume composition of perfume materials having an octanol-water partition coefficient of greater than 2.5 (in logarithmic form to base 10), and typically less than 35% and preferably less than 20% by weight of the total weight of the perfume composition of perfume materials having a octanol-water partition coefficient of greater than 5 (in logarithmic form to base 10).

The octanol-water partition coefficient (P) of a material i.e. the ratio of a material's equilibrium concentration in octanol and water, is well known in the literature as a measure of hydrophobicity and water solubility (see Hansch and Leo, Chemical Reviews, 526 to 616, (1971), 71; Hansch, Quinlan and Lawrence, J. Organic Chemistry, 347 to 350 (1968), 33). High partition coefficient values are more conveniently given in the form of their logarithm to the base 10, log P. While log P values can be measured experimentally i.e. directly, and measured log P data is available for many perfumes, log P values are most conveniently calculated or approximately estimated using mathematical algorithms. There are several recognised calculation or estimation methods available commercially and/or described in the literature (see for example A Leo, Chem.Rev 93(4), 1281-1306, (1993), "Calculating log P oct from structures"). Generally these models correlate highly but may for specific materials produce log P values which differ in absolute terms (by up to 0.5 log units or even more). However, no one model is universally accepted as the most accurate across all compounds. This is particularly true for estimates on materials of high log P (say 4 or greater). In the present specification, log P values are obtained using the estimation software commercially available as 'LogP' from Toronto-based Advanced Chemistry Development Inc (ACD) which is well-known to the scientific community, and accepted as providing high-quality predictions of log P values. References to log P values thus mean values obtained using the ACD software.

The percentage by weight of perfume materials referred to herein is relative to the total weight of perfume materials present in the composition and excludes, for example, the presence of any optional solvents or diluents etc, such as e.g. diethyl phthalate, dipropylene glycol, benzyl benzoate, acetyle tributyl citrate, triethyl citrate, Hercolyn D and isopropyl myristate.

Preferred perfume materials for a perfume composition useful herein, are therefore those perfume materials having an octanol-water partition coefficient (log P) falling within the range 3 to 5. Examples of such perfume materials include the following:

1-(o-tert-butylcyclohexyloxy)butan-2-ol, 1,4-dimethylcyclohexane carboxylic acid methyl ester, 10-iso-propyl-2,7-dimethyl-1-oxaspiro[4.5]3,6-decadiene, 1-methyl-3-(2-methylpropyl)cyclohexanol, 3-(4-tert-butylphenyl)-2-methylpropanal, 4-methyl-3-decen-5-ol, 7,9-dimethylspiro[5,5] undecan-3-one, acetaldehyde ethyl cis-3-hexenyl acetal, acetyl diisoamylene (Q), alcohol C9 (nonanol), aldehyde C9 (nonanal), aldehyde C10 (decanal), aldehyde C11 (undecylenic aldehyde), alicate (Q), allyl caproate, allyl cyclohexyl propionate, allyl heptylate, allyl hexanoate, amyl benzoate, amyl cinnamic alcohol, amyl cinnamic aldehyde, amyl salicylate, amyl valerate, anethole, anther (Q), aurantion (Q), bangalol (Q), beauvertate (Q), benzophenone, benzyl cinnamate, benzyl phenylacetate, benzyl salicylate, borneol, bourgeonal (Q), butyl phenylacetate, calyxol (Q), carvacrol, carvacryl ethyl ether, carveol, cervolide (Q), cineole, Cis-hex-3-enyl salicylate, cistulate (Q), citral, citral dimethyl acetal, citrathal (Q), citronellal, citronellol, citronellyl acetate, citronellyl nitrile, citronellyl oxyacetaldehyde, citronellyl propionate, cressanther (Q), cumin nitrile, cyclamen aldehyde (Q), cyclohexyl salicylate, damascone alpha, dec-4-enal, dec-9-enal, dec-9-enol, dihydroanethole, dihydrocarveol, dihydrocarvone, dihydrojasmone, dihydrolinalol, dihydromyrcenol, dihydromyrcenyl acetate, dihydroterpineol, dihydroterpinyl acetate, dimethylheptanol, diphenyl oxide, diphenylmethane, dodecyl nitrile, dupical (Q), elintaal (Q), empetaal (Q), ethyl cinnamate, ethyl heptylate, ethyl linalol, ethyl nonanoate, ethyl octanoate, ethyl safranate (Q), fenchyl acetate, fenchyl alcohol, florocyclene (Q), frutonile (Q), gardocylene (Q), geraniol, geranyl acetate, geranyl nitrile, geranyl propionate, gyrane (Q), herbanate (Q), hexyl benzoate, hexyl cinnamic aldehyde, hexyl salicylate, inonyl acetate, inonyl propionate, ionones, iso E super (IFF), isoamyl salicylate, isobergamate (Q), isoborneol, isobornyl acetate, isobutyl benzoate, isobutyl cinnamate, isoeugenol, isojasmone, jasmatone (Q), jasmopyran (Q), jessate (Q), kerfoline (Q), lime oxide, linalool, linalyl acetate, linalyl propionate, maceal (Q), mefrosol (Q), menthanyl acetate, menthol, menthyl acetate, methyl chavicol, methyl eugenol, methyl ionones, methyl isoeugenol, methyl nonyl acetaldehyde, methyl octine carbonate, musk R1 (Q), myrcene, neobergamate (Q), nerol, nerolin, neryl acetate, nopyl acetate, octyl acetate, orange terpenes, ortholate (Q), para cresyl phenyl acetate, para-tert-butylcyclohexanol, para-tert-butylcyclohexanyl acetate, pelargene (Q), petiole (Q), phenyl benzoate, phenyl ethyl methyl ethyl carbinol, phenylethyl isobutyrate, phenylethyl methyl ethyl carbinol, phenylethyl phenylacetate, phenylethyl salicylate, pinenes, pivacyclene (Q), rhubafuran (Q), rose oxide, roseacetone, rosyrane (Q), terpinyl acetate, tetrahydrogeraniol, tetrahydrogeranyl acetate, tetrahydrolinalol, tetrahydrolinalyl acetate, tetrahydromyrcenol, thymol, undecanal, undecen-2-nitrile, yara yara.

Materials identified by (Q) above are trade marks or trivial names, and available from Quest International. Materials identified by (IFF) above are trade marks or trivial names, and are available from International Flavours and Fragrances.

The shell capsules may be prepared using a range of conventional methods known to those skilled in the art for making shell capsules such as coacervation, interfacial polymerisation and polycondensation.

The process of coacervation typically involves encapsulation of a generally water-insoluble material by the precipitation of colloidal material(s) onto the surface of droplets of the material. Coacervation may be simple e.g. using one colloid such as gelatin, or complex where two or possibly more colloids of opposite charge, such as gelatin and gum arabic or gelatin and carboxymethyl cellulose, are used under carefully controlled conditions of pH, temperature and concentration. Coacervation techniques are described, e.g. in U.S. Pat. No. 2,800,458, U.S. Pat. No. 2,800,457, GB929403, EP385534 and EP376385.

Interfacial polymerisation produces encapsulated shells from the reaction of at least one oil-soluble wall forming material present in the oil phase with at least one water-soluble wall forming material present in the aqueous phase. A polymerisation reaction between the two wall-forming materials occurs resulting in the formation of covalent bonds at the interface of the oil and aqueous phases to form the capsule wall. An example of a shell capsule produced by this method is a polyurethane capsule.

Polycondensation involves forming a dispersion or emulsion of water-insoluble material e.g. perfume in an aqueous solution of precondensate of polymeric materials under appropriate conditions of agitation to produce capsules of a desired size, and adjusting the reaction conditions to cause condensation of the precondensate by acid catalysis, resulting in the condensate separating from solution and surrounding the dispersed water-insoluble material fill to produce a coherent film and the desired micro-capsules. Polycondensation techniques are described, e.g. in U.S. Pat. No. 3,516,941, U.S. Pat. No. 4,520,142, U.S. Pat. No. 4,528,226, U.S. Pat. No. 4,681,806, U.S. Pat. No. 4,145,184 and GB2073132.

A preferred method for forming shell capsules useful herein is polycondensation, typically to produce aminoplast encapsulates. Aminoplast resins are the reaction products of one or more amines with one or more aldehydes, typically formaldehyde. Non-limiting examples of suitable amines include urea, thiourea, melamine and its derivatives, benzoguanamine and acetoguanamine and combinations of amines. Suitable cross-linking agents (e.g. toluene diisocyanate, divinyl benzene, butane diol diacrylate etc.) may also be used and secondary wall polymers may also be used as appropriate, as described in the prior art e.g. anhydrides and their derivatives, particularly polymers and co-polymers of maleic anhydride as disclosed in WO02/074430. For example, good results have been obtained with aminoplast capsules of mixed resins of urea/formaldehyde, maleic anhydride copolymers and melamine/formaldehyde.

Thus, preferably, the shell capsules are aminoplast capsules, more preferably based on melamine, singly or in combination with other suitable amines, crosslinking agents and secondary polymers.

By modifying process conditions shell capsules of a desired size can be produced in known manner. The shell capsules typically have a mean diameter in the range 1 to 500 microns, preferably 1 to 300 microns, more preferably 1 to 50 microns and most preferably 1 to 10 microns. Preferred sizes for the shell capsules will depend upon their intended use. For example, shell capsules employed in shampoos, rinse conditioners, laundry powders, sheet conditioners and household cleaning products preferably have a mean diameter in the range 1 to 10 microns, most preferably 1 to 5 microns. If necessary, the shell capsules as initially produced may be filtered or screened to produce a product of greater size uniformity.

The shell capsules comprise a coating on the inner surface, the outer surface, or both the inner and outer surfaces of the shell wall. In general, the shell of the capsules useful herein can be considered as made up of a very tight collection of strands of polymer(s) which generally provides a barrier to the encapsulated material. It is thought however, that when the shell capsules are mixed with a surfactant-containing and/or solvent-containing composition e.g. consumer product, the surfactant and/or solvent present in the composition swells the shell and sufficiently separates the strands of polymer to produce pores through which the encapsulated material may pass and/or that the original wall structure contains voids or imperfections through which the encapsulated material may pass. This is a particular problem when the encapsulated material is to some extent surfactant and/or solvent soluble e.g. perfume, as typically, the encapsulated material will be lost to the composition over a relatively short period of time. It has been found by the present inventors, however, that the application of a coating to the inner surface and/or outer surface of the shell wall improves the barrier properties of the shell and thus may enhance retention of the encapsulated materials in surfactant-containing and/or solvent-containing compositions. Without wishing to be bound or limited by theory, it is thought that the coating stiffens the shell to prevent it swelling when in contact with surfactant and/or solvent and/or the coating blocks any pores created when the shell is swollen and/or blocks any voids or pores that were originally present in the shell. A coating may be partial or complete. Preferably, the one or more coatings are complete, so that the shell capsules are thus preferably substantially impermeable.

The application of a coating to the inner surface of the shell capsules may be carried out by a number of methods. One approach involves the use of a suitable material for the coating which is insoluble in the material to be encapsulated, but can be dissolved in a water-soluble solvent e.g. ethanol, carbitol etc., which is miscible with the material to be encapsulated. The approach involves dissolving the coating material, typically a polymer, in the solvent and then dissolving this mixture in the material to be encapsulated. The material to be encapsulated is then emulsified into e.g. a standard aminoplast capsule forming aqueous solution. As the emulsion forms, the solvent is lost to the water and the polymer precipitates out from solution at the surface of the emulsion droplets, forming a film at the interface of water/material to be encapsulated. The normal encapsulation process is then carried out and the coating deposited on the inner surface of the shell. In this case the coating material is typically water-insoluble, but this is not essential.

In a further approach, a material is used that is immiscible with both the material to be encapsulated and water, and is capable of forming a thin film at the water interface. An example of such a material is a silicone. If this material e.g. silicone is a liquid, a shell encapsulate comprising a coating of silicone on the inner surface of the shell can be prepared by dispersing the material to be encapsulated within the silicone and then emulsifying this mixture so that an emulsion is formed where droplets of encapsulated material are surrounded by a thin film of silicone. The encapsulation process is then carried out as normal. Alternatively, a thin film may be formed at the surface by dispersing the material to be encapsulated in water, adding the second material e.g. silicone and allowing it to coat the encapsulating material droplets subsequently.

An inner surface coating is preferably made from a film-forming polymer, e.g. selected from: poly(ethylene-maleic anhydride), polyamine, waxes e.g. carbowax, polyvinylpyrrolidone (PVP) and its co-polymers such as polyvinylpyrrolidone-ethyl acrylate (PVP-EA), polyvinylpyrrolidone-vinyl acrylate, polyvinylpyrrolidone methylacrylate (PVP-MA), polyvinylpyrrolidone/vinyl acetate, polyvinyl acetal, polyvinyl butyral, polysiloxane, polypropylene maleic anhydride), maleic anhydride derivatives and co-polymers of the above, e.g. polyvinyl methyl ether/maleic anhydride. Preferably, the inner wall coating comprises polysiloxane, PVP or PVP co-polymers, more preferably PVP or PVP co-polymers, and even more preferably PVP co-polymers, particularly polyvinylpyrrolidone-methyl acrylate or polyvinylpyrrolidone-ethyl acrylate.

A coating may be applied to the outer surface of a shell capsule by a variety of conventional coating techniques including spraying, fluid bed coating, precipitating etc. For example a coating, typically of polymer, may be precipitated from aqueous solution to condense onto the outer surface of the capsule e.g. in the form of a capsules slurry, with precipitation being caused to occur e.g. by change of temperature, change of pH or addition of salt. The shell capsule to be coated is thus formed in a separate step, prior to the application of the coating to the outer surface of the shell wall. Depending on the composition of the outer surface coating, a coated shell capsule may be prepared for example, by coacervation or polycondensation.

The outer surface coating typically comprises high molecular weight, film-forming polymers, which may optionally be crosslinked. By "high molecular weight" is meant a molecular weight of greater than 5000. The polymer maybe water-soluble or water-insoluble, and is preferably water-soluble. Generally, low molecular weight water-soluble materials (e.g. short chain saccharides) are not suitable. Non-limiting examples of suitable polymers include; polyvinyl alcohol (PVOH), styrene-butadiene latex, gelatin, gum arabic, carboxymethyl cellulose, carboxymethyl hydroxyethyl cellulose, hydroxyethyl cellulose, other modified celluloses, sodium alginate, chitosan, casein, pectin, modified starch, polyvinyl acetal, polyvinyl butyral, polyvinyl methyl ether/maleic anhydride, polyvinyl pyrrolidone (PVP) and its co-polymers (e.g. polyvinylpyrrolidone/vinyl acetate (PVP/VA), poly(vinyl pyrrolidone/dimethylaminoethyl methacrylate) (PVP/DMAEMA) e.g. Gafquat 755N ex ISP Corporation (Gafquat 755N is a Trade Mark), poly(vinyl pyrrolidone/methacrylamidopropyl trimethyl ammonium chloride) e.g. Gafquat HS 100 ex ISP Corporation (Gafquat HS100 is a Trade Mark), melamine-formaldehyde and urea-formaldehyde.

Preferably, the outer surface of the shell is coated with polyvinyl alcohol, PVP or a PVP co-polymer. Polyvinyl alcohol is available in a number of different grades, differing in terms of molecular weight (low, medium or high) and levels of hydrolysis (low, medium, high or fully hydrolysed). Levels of hydrolysis of polyvinyl alcohol can be categorised as follows:

| | |
|---|---|
| Fully hydrolysed: | >98% |
| High hydrolysis (nearly fully hydrolysed): | 95-98% |
| Medium hydrolysis: | 85-94% |
| Low hydrolysis: | <85% |

Molecular weights of polyvinyl alcohol can be categorised as follows:

| | |
|---|---|
| Low MW | <50,000 |
| Medium MW | >50,000 and <125,000 |
| High MW | >125,000 |

While polyvinyl alcohol having a high hydrolysis level and high molecular weight is likely to give better barrier properties, such materials can be harder to work with: the viscosity of the reaction mixture increases with the molecular weight of the polyvinyl alcohol and use of high molecular weight material tends to produce mixtures that have undesirably high viscosities; further, fully hydrolysed polyvinyl alcohol can be difficult to work with. Polyvinyl alcohol having a medium level of hydrolysis and low molecular weight is current favoured in terms of overall properties and behaviour. Polyvinyl alcohol is commercially available from a number of suppliers including Celanese Chemicals (under the Trade Mark Celvol) and Nippon Gohsei (under the Trade Mark Gohsenol). Typical materials useful in the invention include the following:

| | |
|---|---|
| Gohsenol NL-05, Celvol 305, Celvol 103 | fully hydrolysed (>98%), low MW |
| Gohsenol GL-05, Celvol 203 | 87-89% hydrolysed, low MW |
| Gohsenol GL-23, Celvol 540 | 87-89% hydrolysed, high MW |
| Gohsenol KL-05 | 78-82% hydrolysed, low MW |

Good results have been obtained with PVOH (high MW, high hydrolysis) and PVP-DMAEMA, and these materials are currently favoured.

The coating (inner and/or outer) may be cross-linked in known manner, e.g. by interfacial cross-linking.

A shell capsule useful herein may comprise more than one coating on the outer surface of the shell.

Coated shell capsules typically have a wall thickness in the range 0.01 to 30 microns, preferably 0.01 to 5 microns, more preferably 0.03 to 1 microns, most preferably 0.03 to 0.5 microns. The wall thickness may be regulated and controlled according to the encapsulate size and by varying the relative proportions of coating and shell polymer.

The weight ratio of coating to shell wall is typically in the range of 0.01 to 10:1, preferably 0.1:1 to 10:1, more preferably 0.1:1 to 3:1.

Typically, the weight ratio of polymer shell wall material to encapsulated material is in the range 1:10 to 3:2 and preferably in the range 1:10 to 1:2. The coating on the inner surface and/or outer surface will increase these weight ratios.

The solvent of the composition may be selected from those well known to those skilled in the art, and include propylene glycol, dipropylene glycol, diethylene glycol monoethyl ether, isopropyl myristate, ethanol, isopropyl alcohol, butyl alcohol, diethylene glycol monobutyl ether, glycerin, dipropylene glycol mono-n-butyl ether, orange oil and mineral oil.

The surfactant of the composition may be selected from those well known to those skilled in the art, including anionic surfactants, nonionic surfactants, cationic surfactants, amphoteric surfactants, zwitterionic surfactants and mixtures thereof. Appropriate surfactant(s) will depend on the nature of the composition, as discussed above, as is known to those skilled in the art. Anionic surfactants include soaps, synthetic detergent surfactants, sulphate surfactants, sulphonate surfactants and N-acylamino surfactants. Nonionic surfactants include alkyl phenol ethoxylates, polyethylene glycol/polypropylene glycol block copolymers, fatty alcohol and fatty acid ethoxylates, long chain tertiary amine oxides, long chain tertiary phosphine oxides, long chain dialkyl sulphoxides, alkyl polysaccharides and polyethylene glycol glyceryl fatty esters. For further details of surfactants see, e.g., WO 96/12468 page 8 to 21.

The weight ratio of solvent/surfactant: capsules in the composition is conveniently in the range 100:1 to 5:1.

Incorporation of the capsules into compositions containing solvent and/or surfactant may be conveniently achieved by addition of the capsule slurry by a variety of mixing techniques that are well known to those skilled in the art. Alternatively, addition to substantially dry compositions (e.g laundry powders) can be achieved by first drying the capsule slurry (e.g. by spray-drying) followed by dry mixing.

As discussed above, the coated shell capsules described herein, possess improved impermeability properties in surfactant-containing and/or solvent-containing compositions compared with the uncoated shell encapsulates of the prior art. Thus, advantageously, when shell capsules comprising a coating on the inner surface and/or outer surface of the shell are incorporated in surfactant-containing and/or solvent-containing compositions, the coated shell capsules demonstrate improved retention of the encapsulated material and thus demonstrate improved in-storage stability. Coated shell capsules comprising encapsulated material such as perfume, when incorporated in a shampoo, typically prevent perfume from leaching from the encapsulates for weeks and possibly months. By contrast, perfume-containing uncoated shell capsules of the prior art tend to leach perfume from the encapsulates over days, e.g. at 45° C.

In a further aspect, the present invention provides capsules comprising encapsulated perfume, the perfume being encapsulated within an aminoplast capsule which comprises a coating of polyvinyl alcohol, polyvinyl pyrrolidone or a co-polymer polyvinyl pyrrolidone (preferably PVP/DMAEMA) on the outer surface of the shell and/or a coating of a film-forming polymer (preferably polyvinyl pyrrolidone-ethyl acrylate) on the inner surface.

BRIEF DESCRIPTION OF THE DRAWINGS

FIG. 1 shows transmission light micrographs illustrating the relative stability of the capsules in shampoos BR2 and B4. Perfume retention in shampoo B4 is clearly enhanced.

The invention will be further described, by way of illustration, in the following examples.

EXAMPLES

The following formulations are used in the Examples.

Perfume A—this perfume is used in all the capsule examples below and is supplied by Quest International under the code HW 4180B.

Shampoo Base B—the following hair shampoo formulation is used in Comparative Examples 1, 2 and 4 below:

| Ingredient | % by weight |
| --- | --- |
| Sodium lauryl ether (2 mole) sulphate | 9.6 |
| Ammonium lauryl ether (2 mole) sulphate | 4.5 |
| Sodium chloride | 2.0 |
| Euperlan PK 3000 AM* | 1.0 |
| Citric acid | q.s. to give pH 6.0-6.5 |
| Preservative | q.s. |
| Water | balance to 100% |

*ex Cognis, Germany (Euperlan is a Trade Mark)

Rinse Conditioner Base C—the following rinse conditioner formulation is used in Comparative Example 3 below:

| Ingredient | % by weight |
| --- | --- |
| Rewoquat WE18* | 16.7 |
| CaCl$_2$ (10% aq) | 0.5 |
| Formaldehyde | 0.1 |
| Distilled water | to 100.0 |

*Rewoquat WE18 is a dehydrogenated tallowethyl hydroxyethylmonium methosulphate (Rewoquat is a Trade Mark) ex Goldschmidt (a division of Degussa AG).

Preparation

The water is heated to 50° C. Separately, Rewoquat is heated to 50° C. and then slowly dispersed into the water and stirred until cool. Formaldehyde is then added and mixed well. The calcium chloride solution is slowly added and mixed for five minutes.

Reference Example 1

The following example illustrates the formation of a standard polycondensation microcapsule based on melamine/formaldehyde polymer. A solution of 66 g of a 10% solution of Versa TL502 (a sodium polystyrene sulphonate) from National Starch and Chemical Company, Bridgewater, USA (Versa TL is a Trade Mark) was added to 130 g of distilled water and adjusted to a pH of 4.5 using a 20% solution of sodium hydroxide. Separately, a 40% solution of melamine in 37% formaldehyde was prepared. 100 g of perfume A (the "Internal Phase") were then added to the sodium polystyrene sulphonate solution, which was maintained under continuous agitation to allow the formation of an emulsion of the perfume in water. 72 g of the melamine formaldehyde solution were then added. The emulsion was heated to 55° C. in a water bath and held there for two hours under continuous agitation and allowed to cool overnight. The capsules produced by this method had a mean particle size of 8 μm with a perfume content of 27% in the capsule slurry.

Example 1

This example illustrates the formation of a coating of polyvinyl pyrrolidone on the inner surface of a capsule wall. 10 g of polyvinylpyrrolidone (Luviskol K-90, ex BASF) were dissolved in 90 g of isopropyl alcohol. 12 g of this resulting solution was then dissolved in 88 g of perfume A. The resultant mixture was then agitated and warmed to 35° C. for eight hours to form a clear homogeneous solution. This solution was then used as the Internal Phase to produce capsules by the method of Reference Example 1. The resultant capsules had a mean particle size of 6 μm with a perfume content of 24.2% in the capsule slurry.

Example 2

This example illustrates the formation of a coating of silicone fluid on the inner surface of a capsule wall. 390 g of perfume A was added to a laboratory mixing vessel and mixed with 24 g of polysiloxane fluid (Dow Corning Silicone DC200/100). This mixture was then emulsified with a Silverson mixer for one hour. 100 g of the resultant emulsion was then used as the Internal Phase to produce capsules by the method of Reference Example 1. The resultant capsules had a mean particle size of 10 μm with a perfume content of 25.6% in the capsule slurry.

Example 3

The following example illustrates the formation of a polyvinylpyrrolidone (PVP) coating on the inner surface of a capsule wall, further strengthened by interfacial crosslinking. Capsules were prepared using the formulation illustrated in Example 1. However, the encapsulation process was modified by the inclusion of 0.3 g of a crosslinking agent, toluene diisocyanate, in the PVP pre-solution. The capsules produced in this example had a mean particle size of 4 μm with a perfume content of 24.3% in the capsule slurry.

Comparative Example 1

This example illustrates the enhanced perfume retention properties of capsules according to one approach of the invention (having a coating on the inner surface of a capsule wall) compared to standard capsules. The capsule slurries of Reference Example 1 and Examples 1-3 were mixed into unperfumed shampoo base B to produce the following formulations, each containing 0.15 wt % perfume (all expressed as percent by weight):

|  | Shampoo Code | | | |
| --- | --- | --- | --- | --- |
|  | BR1 | B1 | B2 | B3 |
| Shampoo base B | 99.444 | 99.380 | 99.414 | 99.383 |
| Reference Example 1 | 0.556 | — | — | — |
| Example 1 | — | 0.620 | — | — |
| Example 2 | — | — | 0.586 | — |
| Example 3 | — | — | — | 0.617 |

The shampoos were then stored in glass jars for one month at 37° C. and examined by transmission light microscopy to determine the degree of perfume loss from the capsules. The capsules in shampoo BR1 were found to be completely empty whilst the capsules in shampoos B1, B2 and B3 were all found to contain significant levels of perfume, thus illustrating the utility of the invention.

Example 4

This example illustrates the formation of a coating of polyvinyl alcohol on the outer surface of a capsule wall using capsules of reference Example 1. Perfume containing microcapsules were prepared using the method outlined in Reference Example 1. At the completion of the 2 hours at 55° C., the microcapsule emulsion was heated to 80° C. Simultaneously, a 20% solution of polyvinyl alcohol (Celvol 203 (low molecular weight, 87-98% hydrolysed), ex Celanese Chemicals) in water was prepared and heated to 80° C. 60 g of the polyvinyl alcohol solution were added to the warmed microcapsule slurry and agitation continued for 24 hours during which time the mixture cools slowly. The polyvinyl alcohol precipitates onto the microcapsules thus forming a coating. The final microcapsule slurry had a perfume content of 23.4%.

Example 5

This example illustrates the formation of a coating of polyvinyl acetal on the outer surface of a capsule wall using capsules of reference example 1. Perfume containing microcapsules are prepared using the method outlined in Reference Example 1. At the completion of the 2 hours at 55° C., the microcapsule emulsion was heated to 80° C. Simultaneously, a 20% solution of polyvinyl alcohol (Celvol 203, ex Celanese Chemicals) in water was prepared and heated to 80° C. 60 g of the polyvinyl alcohol solution were added to the warmed microcapsule slurry. The pH was then adjusted to 4.5 using sulphuric acid and 6 g of 37% formaldehyde was added to the mixture. Agitation was continued for 24 hours during which time the mixture cools slowly. During this time, polyvinyl acetal is formed and precipitates onto the microcapsules forming a coating. The final microcapsule slurry had a perfume content of 23.0%.

Example 6

This example illustrates the formation of a coating of a water-insoluble polyvinyl pyrrolidone/vinyl acetate copolymer on the outer surface of a capsule wall using reference example 1. Perfume containing microcapsules are prepared using the method outlined in Reference Example 1. At the completion of the 2 hours at 55° C., the microcapsule emulsion is maintained at 55° C. Simultaneously, a 10% solution of polyvinyl pyrrolidone/vinyl acetate copolymer (ISP S630 from ISP Corporation) in isopropyl alcohol was prepared and heated to 55° C. 40 g of the polyvinyl pyrrolidone/vinyl acetate copolymer solution were added to the warmed microcapsule slurry and agitation was continued for 4 hours at 55° C. The mixture was then allowed to cool under agitation for a further 24 hours. The polyvinyl pyrrolidone/vinyl acetate copolymer precipitates onto the microcapsules as the isopropyl alcohol evaporates from the mixture. The final microcapsule slurry contained 26.8% perfume.

Example 7

This example illustrates the formation of a coating of carboxymethyl cellulose (CMC) on the outer surface of a capsule wall using capsules of reference example 1. A 10% aqueous solution of carboxymethyl cellulose (Finea 10 (Finea is a Trade Mark) was prepared by mixing and heating until a clear homogeneous solution was formed. Meanwhile, the capsule slurry of Reference Example 1 was spray-dried to form a free-flowing powder using a laboratory spray dryer (Buchi Model 190, ex Buchi Labortechnik AG). The resultant powder was then charged into a laboratory fluid bed dryer (Glatt Model TR 5) and the capsules were coated by spraying of the CMC solution using standard fluid bed coating techniques to achieve a coating thickness of 0.4 μm. The resultant capsules were analysed and found to contain 79% perfume.

Comparative Example 2

This example illustrates the enhanced perfume retention properties of capsules according to another approach of the invention (having a coating on the outer surface of a capsule wall) compared to standard capsules. The capsule slurries of Reference Example 1 and Examples 4-7 were mixed into unperfumed shampoo base B to produce the following formulations, each containing 0.2 wt % perfume (all expressed as percent by weight):

|  | Shampoo Code | | | | |
|---|---|---|---|---|---|
|  | BR2 | B4 | B5 | B6 | B7 |
| Shampoo base B | 99.259 | 99.145 | 99.130 | 99.254 | 99.747 |
| Reference Example 1 | 0.741 | — | — | — | — |
| Example 4 | — | 0.855 | — | — | — |
| Example 5 | — | — | 0.870 | — | — |
| Example 6 | — | — | — | 0.746 | — |
| Example 7 | — | — | — | — | 0.253 |

The shampoos were then stored in glass jars for one month at 37° C. and examined by transmission light microscopy to determine the degree of perfume loss from the capsules. The capsules in shampoo BR2 were found to be completely empty whilst the capsules in shampoos B4, B5, B6 and B7 were all found to contain significant levels of perfume, thus illustrating the utility of the invention.

FIG. 1 shows transmission light micrographs illustrating the relative stability of the capsules in shampoos BR2 and B4. Perfume retention in shampoo B4 is clearly enhanced.

Comparative Example 3

This example illustrates the enhanced perfume retention properties of capsules according to the invention compared to standard capsules. The capsule slurries of Reference Example 1 and Examples 1, 4, 6 and 7 were mixed into unperfumed rinse conditioner base C to produce the following formulations, each containing 0.2 wt % perfume (all expressed as percent by weight):

|  | Conditioner Code | | | | |
|---|---|---|---|---|---|
|  | CR1 | C1 | C4 | C6 | C7 |
| Conditioner base C | 99.259 | 99.174 | 99.145 | 99.254 | 99.747 |
| Reference Example 1 | 0.741 | — | — | — | — |
| Example 1 | — | 0.826 | — | — | — |
| Example 4 | — | — | 0.855 | — | — |
| Example 6 | — | — | — | 0.746 | — |
| Example 7 | — | — | — | — | 0.253 |

The rinse conditioners were then stored in glass jars for one month at 37° C. and examined by transmission light microscopy to determine the degree of perfume loss from the capsules. The capsules in conditioner CR1 were found to be completely empty whilst the capsules in conditioners C1, C4, C6 and C7 were all found to contain significant levels of perfume, thus illustrating the utility of the invention.

Reference Example 2

This example illustrates the formation of a typical complex coacervate encapsulate. 25 g of acid-treated gelatin (isoelectric point 8, gel strength 180 g Bloom) and 2.5 g of carboxymethyl cellulose (Blanose Gum, ex ISP Corporation, New Jersey, USA) were added to 700 g water and mixed with heating at 60° C. until a clear homogeneous solution was formed. The pH was then adjusted to 5.5 with a 5% aqueous solution of sodium hydroxide and then cooled to 10° C. 100 g of perfume A was then added to this solution whilst mixing was maintained to generate an emulsion of perfume. 25 g of 10% aqueous formaldehyde was then mixed into the emulsion and left to stand for 15 minutes. The pH of the emulsion was then adjusted to 10 by dropwise addition of a 10% aqueous solution of NaOH, causing the formation of hardened microcapsules. The resulting slurry was analysed and found to contain 11.7% perfume by weight. The capsules produced by this method had a mean particle size of 12 μm.

Example 8

This example illustrates the formation of a coating of polyvinyl alcohol on the outer surface of a capsule using capsules of reference example 2. Perfume containing microcapsules are prepared using the method outlined in Reference Example 2. At the completion of hardening of the capsule walls, the microcapsule emulsion was heated to 80° C. Simultaneously, a 20% solution of polyvinyl alcohol (Celvol 203, ex Celanese Chemicals) in water was prepared and heated to 80° C. 60 g of the polyvinyl alcohol solution were then added to the warmed microcapsule slurry and agitation continued for 24 hours during which time the mixture cooled slowly. The polyvinyl alcohol precipitates onto the microcapsules thus forming a coating. The microcapsule slurry was measured to have a final perfume content of 11.0%.

Example 9

This example illustrates the formation of a coating of polyvinyl acetal on the outer surface of a capsule using capsules of reference example 2. Perfume containing microcapsules are prepared using the method outlined in Reference Example 2. At the completion of hardening of the capsule walls, the microcapsule emulsion was heated to 80° C. In parallel, a 20% solution of polyvinyl alcohol (Celvol 203, ex Celanese Chemicals) in water was prepared and heated to 80° C. 60 g of the polyvinyl alcohol solution was added to the warmed microcapsule slurry and pH adjusted to 4.5 using sulphuric acid. 6 g of 37% formaldehyde were then added to the mixture. Agitation was continued for 24 hours during which time the mixture cools slowly. The polyvinyl acetal is formed and precipitates onto the microcapsules. The final microcapsule slurry contained 10.8% perfume.

Example 10

This example illustrates the formation of a coating of polyvinyl pyrrolidone/vinyl acetate copolymer on the outer surface of a capsule. Perfume containing microcapsules are prepared using the method outlined in Reference Example 2. At the completion of hardening of the capsule walls, the microcapsule emulsion was heated to 55° C. A 10% solution of polyvinyl pyrrolidone/vinyl acetate copolymer (ISP S630, ex ISP Corporation) in isopropyl alcohol was prepared and heated to 55° C. 40 g of the polyvinyl pyrrolidone/vinyl acetate copolymer solution were added to the warmed microcapsule slurry and agitation continued for 4 hours at 55° C. The mixture was then allowed to cool under agitation for a further 24 hours. The polyvinyl pyrrolidone/vinyl acetate copolymer was precipitated onto the microcapsules as the isopropyl alcohol evaporates from the mixture. The measure perfume level in the capsule slurry was 11.6%.

Example 11

This example illustrates the formation of a coating of carboxymethyl cellulose (CMC) onto the outer surface of a capsule using capsules of reference example 2. A 10% aqueous solution of carboxymethyl cellulose (Finea 10) was prepared by mixing and heating until a clear homogeneous solution was formed. Meanwhile, the capsule slurry of Reference Example 2 was spray-dried to form a free-flowing powder using a laboratory spray dryer (Buchi Model 190). The resultant powder was then charged into a laboratory fluid bed dryer (Glatt Model TRS) and the capsules were coated by spraying of the CMC solution using standard fluid bed coating techniques to achieve a coating thickness of 0.6 μm. The resultant capsules were analysed and found to contain 16% perfume.

Comparative Example 4

This example illustrates the enhanced perfume retention properties of capsules according to the approach of the invention (having a coating on the outer surface of a capsule wall) compared to standard capsules. The capsule slurries of Reference Example 2 and Examples 8-10 were mixed into unperfumed shampoo base B to produce the following formulations (all expressed as percent by weight):

|  | Shampoo Code | | | |
| --- | --- | --- | --- | --- |
|  | BR2 | B8 | B9 | B10 |
| Shampoo base B | 98.29 | 98.18 | 98.15 | 98.28 |
| Reference Example 2 | 1.71 | — | — | — |
| Example 8 | — | 1.82 | — | — |
| Example 9 | — | — | 1.85 | — |
| Example 10 | — | — | — | 1.72 |

The shampoos were then stored in glass jars for one week at 37° C. and examined by transmission light microscopy to determine the degree of perfume loss from the capsules. The capsules in shampoo BR2 were found to be completely empty whilst the capsules in shampoos B8, B9 and B10 were found to contain significant levels of perfume, thus illustrating the utility of the invention.

Example 12

This example illustrates the formation of a capsule with coatings on both the inner and outer surfaces of the capsule wall. 10 g of polyvinylpyrrolidone (Luviskol K-90, ex BASF) were dissolved into 90 g of isopropyl alcohol. 12 g of this resulting solution were then dissolved in 80 g of perfume A. The resultant mixture was then agitated and warmed to 35° C. for eight hours to form a clear homogenous solution. This solution was then used as the Internal Phase to produce capsules by the method of Reference Example 1. At the completion of the 2 hours at 55° C., the microcapsule emulsion was heated to 80° C. Simultaneously, a 20% solution of polyvinyl alcohol (Celvol 203, ex Celanese Chemicals) in water was prepared and heated to 80° C. 60 g of the polyvinyl alcohol solution were added to the warmed microcapsule slurry and agitation continued for 24 hours during which time the mixture cooled slowly. The polyvinyl alcohol precipitates onto the microcapsules thus forming a coating and hence creating an outer wall. The final microcapsule slurry had a perfume content of 22.3%.

Reference Example 3

The following example illustrates the formation of a microcapsule based on mixed resins of urea/formaldehyde, poly (propylene/maleic anhydride) and melamine/formaldehyde polymers. 100 g of a 10 wt % solution of polypropylene maleic anhydride) was mixed with 200 g of distilled water and adjusted to a pH of 4.5 using a 20 wt % solution of sodium hydroxide. Separately, a 60 wt % aqueous solution of methylol melamine (Resimene 814, ex Monsanto—Resimene 814 is a Trade Mark) was prepared. 35 g of this methylol melamine solution was added to 150 g of the polypropylene maleic anhydride) solution in a laboratory mixing vessel and stirred with a standard laboratory paddle mixer. A solution of 20 g of water and 9 g of urea was prepared in a beaker with stirring by heating to 40° C. for 1 hour. Into this urea solution 0.5 g of resorcinol was dissolved. The urea solution was then added to the above methylol melamine solution and the combined mix was stirred and cooled over 24 hours. 150 g of perfume A (the "Internal Phase") was then added to the combined solution which was maintained under continuous agitation to allow the formation of an emulsion of the perfume. The emulsion was then heated to 55° C. in a water bath and held there for two hours under continuous agitation to allow capsule formation. The capsules produced by this method had a mean particle size of 3 μm with a perfume content of approximately 23 wt % in the capsule slurry.

Example 13

This example illustrates the formation of a coating of polyvinyl pyrrolidone/methyl acrylate co-polymer (PVP-MA) on the inner surface of a capsule wall. 15 g of PVP-MA were dissolved in 90 g of isopropyl alcohol. 10 g of this resulting solution was then dissolved in 90 g of perfume A. The resultant mixture was then agitated and warmed to 35° C. for four hours to form a clear homogeneous solution. This solution was then used as the Internal Phase to produce capsules by the method of Reference Example 3. The resultant capsules had a mean particle size of 7 μm with a perfume content of approximately 20% in the capsule slurry.

Example 14

This example illustrates the formation of a coating of polyvinyl pyrrolidone/dimethylaminoethyl methacrylate copolymer (PVP/DMAEMA) on the outer surface of a capsule. Perfume containing microcapsules were prepared using the method outlined in Reference Example 3. At the completion of hardening of the capsule walls, the microcapsule emulsion was heated to 55° C. 25 g of the PVP/DMAEMA copolymer solution (Gafquat 755N ex ISP Corporation, New Jersey, USA) were added to the warmed microcapsule slurry and agitation continued for 4 hours at 55° C. The mixture was then allowed to cool under agitation for a further 24 hours, causing the PVP/DMAEMA copolymer to precipitate onto the microcapsules. The resultant capsules had a mean particle size of 3 µm and a measured perfume level in the capsule slurry of 21.8%.

Example 15

This example illustrates the formation of a coating of polyvinyl pyrrolidone/methyl acrylate co-polymer (PVP-MA) on the inner surface of a capsule wall and a coating of polyvinyl pyrrolidone/dimethylaminoethyl methacrylate copolymer (PVP/DMAEMA) on the outer surface. Perfume containing microcapsules were prepared using the method outlined in Example 13. At the completion of the hardening of the capsule walls, the microcapsule emulsion was heated to 55° C. 35 g of PVP/DMAEMA copolymer solution (Gafquat 440 ex ISP Corporation, New Jersey, USA) were added to the warmed microcapsule slurry and agitation continued for 5 hours at 55° C. The mixture was then allowed to cool under agitation for a further 24 hours, causing the PVP/DMAEMA copolymer to deposit onto the microcapsules. The resultant capsules had a mean particle size of approximately 7 µm and a measured perfume level in the slurry of 18.0%.

Reference Example 4

The following example illustrates the formation of a microcapsule based on melamine/formaldehyde resin with two secondary polymers of 2-acrylamido-2-methyl propane sulphonic acid and poly(propylene maleic anhydride). 42 g of a 10 wt % solution of poly(propyelene maleic anhydride) was added to 108 g of distilled water and adjusted to a pH of 4.5 using a 20 wt % solution of sodium hydroxide. Separately, a 60 wt % aqueous solution of methylol melamine (Resimene 814, ex Monsanto) was prepared. 45 g of this solution was added to 138 g of distilled water in a laboratory mixing vessel and stirred with a standard laboratory paddle mixer. A solution of 29 g of water and 4 g of 2-acrylamido-2-methyl propane sulphonic acid (AMPS monomer) was prepared in a beaker with stirring by heating to 55° C. for 3 hours. The AMPS monomer solution was then added to the above methyol melamine solution and the combined mix was stirred and cooled over 24 hours. 165 g of perfume A (the "Internal Phase") was then added to the combined solution which was maintained under continuous agitation to allow the formation of an emulsion of the perfume. By dropwise addition, 0.2 g of toluene di-isocyanate was added. The emulsion was then heated to 55° C. in a water bath and held there for eight hours under continuous agitation to allow capsule formation. The capsules produced by this method had a mean particle size of 3 µm with a perfume content of approximately 31% in the capsule slurry.

Example 16

This example illustrates the formation of a coating of polyvinyl pyrrolidone/ethyl acrylate (PVP-EA) on the inner surface of a capsule wall. 14 g of PVP-EA were dissolved in 86 g of isopropyl alcohol. 10 g of this resulting solution was then dissolved in 90 g of perfume A. The resultant mixture was then agitated and warmed to 35° C. for three hours to form a clear homogeneous solution. This solution was then used as the Internal Phase to produce capsules by the method of Reference Example 4. The resultant capsules had a mean particle size of 5 µm with a perfume content of approximately 28% in the capsule slurry.

Example 17

This example illustrates a coating of polyvinyl pyrrolidone/ethyl acrylate (PVP-EA) on the inner surface of a capsule wall combined with a coating of polyvinyl alcohol (PVOH) on the outer surface of the capsule wall. Perfume containing microcapsules are prepared using the method described in Example 16. At the completion of the capsule forming process, the microcapsule emulsion was heated to 80° C. Simultaneously, a 20% solution of polyvinyl alcohol (Celvol 203, ex Celanese Chemicals) in water was prepared and heated to 80° C. 70 g of the polyvinyl alcohol solution were then added to the warned microcapsule slurry and agitation continued for 24 hours during which time the mixture cooled slowly. The polyvinyl alcohol precipitates onto the microcapsules thus forming a coating. The microcapsule slurry was measured to have a final perfume content of 26.2%.

Example 18

This example illustrates the preparation of capsules in a substantially water-free form. Capsule slurry was prepared using the method of example 14. The capsule slurry was then spray-dried to form a free-flowing powder using a laboratory spray dryer (Buchi Model 190).

The invention claimed is:

1. A composition comprising a perfume encapsulated within shell capsules, each capsule being an aminoplast capsule comprising an encapsulating wall having an inner surface and an outer surface, with a coating of film-forming polymer on the inner surface of the shell wall and a coating of polyvinyl alcohol, polyvinylpyrrolidone or copolymer of polyvinylpyrrolidone on the outer surface of the shell wall; and surfactant and/or solvent wherein the film-forming polymer coating on the inner surface of the shell wall is selected from the group consisting of: poly(ethylene-maleic anhydride), polyamine, polyvinylpyrrolidone (PVP) polyvinylpyrrolidone-ethyl acrylate (PVP-EA), polyvinylpyrrolidone-vinyl acrylate, polyvinylpyrrolidone methylacrylate (PVP-MA), polyvinylpyrrolidone/vinyl acetate, polyvinyl acetal, polyvinyl butyral, polysiloxane, poly(propylene/maleic anhydride), maleic anhydride derivatives and polyvinyl methyl ether/maleic anhydride.

2. A composition according to claim 1, wherein the composition is a consumer product.

3. A composition according to claim 2, wherein the product is a water-based product.

4. A composition according to claim 1, wherein the encapsulated perfume comprises a first perfume which is at least partially soluble in the surfactant and/or solvent of the composition.

5. A composition according to claim 1, wherein the perfume is in the form of a perfume composition, which comprises at least 80% by weight of the total weight of the perfume composition of perfume materials having an octanol-water partition coefficient of greater than 2.5 (in logarithmic form to base 10).

6. A composition according to claim 5, wherein less than 35% by weight of the total weight of the perfume composition comprises perfume materials having an octanol-water partition coefficient of greater than 5 (in logarithmic form to base 10).

7. A composition according to claim 1, wherein the shell capsules are prepared by coacervation, interfacial polymerisation or polycondensation.

8. A composition according to claim 1, wherein the shell capsules are aminoplast capsules, based on melamine, singly or in combination with other suitable antes, crosslinking agents and secondary polymers.

9. A composition according to claim 1, wherein the aminoplast capsules comprise a mixed resin of urea/formaldehyde, maleic anhydride copolymer(s) and melamine/formaldehyde polymers.

10. A composition according to claim 1, wherein the shell capsules have a diameter in the range 1 to 500 microns.

11. A composition according to claim 1, wherein the film-forming polymer on the inner surface of the shell wall is selected from the group consisting of: polyvinylpyrrolidone (PVP), polyvinylpyrrolidone-ethyl acrylate (PVP-EA), polyvinylpyrrolidone-vinyl acrylate, polyvinylpyrrolidone methylacrylate (PVP-MA) and polyvinylpyrrolidone/vinyl acetate.

12. A composition according to claim 1, wherein the polymer of the outer coating is selected from the group consisting of polyvinyl alcohol, polyvinyl pyrrolidone (PVP), polyvinylpyrrolidone/vinyl acetate (PVPNA), poly(vinyl pyrrolidone/dimethyaminoethyl methacrylate) (PVP/DMAEMA), and poly(vinyl pyrrolidone/methacrylamidopropyl trimethyl ammonium chloride).

13. A composition according to claim 1, wherein the coated shell capsules have a wall thickness in the range of 0.01 to 30 microns.

14. A composition according to claim 1, wherein the weight ratio of shell wall material to encapsulated perfume is in the range of 1:10 to 3:2.

15. A composition according to claim 1, wherein the weight ratio of solvent/surfactant: capsules in the composition is in the range 100:1 to 5:1.

16. Capsules comprising encapsulated perfume, the perfume being encapsulated within shell capsules, each capsule being an aminoplast capsule comprising an encapsulating wall having an inner surface and an outer surface, with a coating of film-forming polymer on the inner surface of the shell wall and a coating of polyvinyl alcohol, polyvinylpyrrolidone or copolymer of polyvinylpyrrolidone on the outer surface of the shell wall wherein the film-forming polymer coating the inner surface of the shell wall is selected from the group consisting of: poly(ethylene-maleic anhydride), polyamine, polyvinylpyrrolidone (PVP), polyvinylpyrrolidone-ethyl acrylate (PVP-EA), polyvinylpyrrolidone-vinyl acrylate, polyvinylpyrrolidone methylacrylate (PVP-MA), polyvinylpyrrolidone/vinyl acetate, polyvinyl acetal, polyvinyl butyral, polysiloxane, polypropylene/maleic anhydride), maleic anhydride derivatives and polyvinyl methyl ether/maleic anhydride.

17. Capsules according to claim 16, wherein the encapsulated perfume comprises a first perfume which is at least partially soluble, in surfactant solution and/or solvent.

18. Capsules according to claim 16, wherein the perfume is in the form of a perfume composition, which comprises at least 80% by weight of the total weight of the perfume composition of perfume materials having an octanol-water partition coefficient of greater than 2.5 (in logarithmic form to base 10).

19. Capsules according to claim 18, wherein less than 35% by weight of the total weight of the perfume composition comprises perfume materials having an octanol-water partition coefficient of greater than 5 (in logarithmic form to base 10).

20. Capsules according to claim 16, wherein the shell capsules are prepared by coacervation, interfacial polymerisation or polycondensation.

21. Capsules according to claim 16, wherein the shell capsules are aminoplast capsules, based on melamine, singly or in combination with other suitable amines, crosslinking agents and secondary polymers.

22. Capsules according to claim 16, wherein the aminoplast capsules comprise a mixed resin of urea/formaldehyde, maleic anhydride copolymer(s) and melamine/formaldehyde polymers.

23. Capsules according to claim 16, wherein the shell capsules have a diameter in the range 1 to 500 microns.

24. Capsules according to claim 16, wherein the polymer is selected from the group consisting of: polyvinylpyrrolidone (PVP), polyvinylpyrrolidone-ethyl acrylate (PVP-EA), polyvinylpyrrolidone-vinyl acrylate, polyvinylpyrrolidone methylacrylate (PVP-MA), and polyvinylpyrrolidone/vinyl acetate.

25. Capsules according to claim 16, wherein the polymer of the coating on the outer surface is selected from the group consisting of: polyvinyl alcohol, polyvinyl pyrrolidone (PVP), polyvinylpyrrolidone/vinyl acetate (PVPNA) polyvinyl pyrrolidone/dimethyaminoethyl methacrylate) (PVP/DMAEMA), and polyvinyl pyrrolidone/methacrylamidopropyl trimethyl ammonium chloride).

26. Capsules according to claim 16, wherein the coated shell capsules have a wail thickness in the range 0.01 to 30 microns.

27. Capsules according to claim 16, wherein the weight ratio of shell wall material to encapsulated material is in the range 1:10 to 3:2.

28. Capsules comprising encapsulated perfume, the perfume being encapsulated within an aminoplast capsule which comprises a coating of polyvinyl alcohol, polyvinyl pyrrolidone or a co-polymer of polyvinyl pyrrolidone on the outer surface of the shell, and a coating of a film-forming polymer on the inner surface of the shell, said coating of film-forming polymer comprising one or more polymers selected from the group consisting of: poly(ethylene-maleic anhydride), polyamine, polyvinylpyrrolidone (PVP), polyvinylpyrrolidone-ethyl acrylate (PVP-EA), polyvinylpyrrolidone-vinyl acrylate, polyvinylpyrrolidone methylacrylate (PVP-MA), polyvinylpyrrolidone/vinyl acetate, polyvinyl acetal, polyvinyl butyral, polysiloxane, poly(propylene/maleic anhydride), maleic anhydride derivatives and polyvinyl methyl ether/maleic anhydride.

29. Capsules according to claim 28, wherein each capsule includes a coating on the outer surface of the shell comprising polyvinyl alcohol and/or poly(vinyl pyrrolidone/dimethylaminoethyl methacrylate).

30. Capsules according to claim 28, wherein the capsules have a diameter in the range 1 to 50 microns.

31. Capsules according to claim 28, wherein the perfume is in the form of a perfume composition, which comprises at least 80% by weight of the total weight of the perfume composition of perfume materials having an octanol-water partition coefficient of greater than 2.5 (in logarithmic form to base 10).

32. Capsules according to claim 31, wherein less than 35% by weight of the total weight of the perfume composition comprises perfume materials having an octanol-water partition coefficient of greater than 5 (in logarithmic form to base 10).

33. A composition comprising a perfume encapsulated within shell capsules, each capsule being an aminoplast capsule comprising an encapsulating wall having an inner surface and an outer surface, with a coating of film-forming polymer on the inner surface of the shell wall and a coating on the outer surface of the shell wall; and surfactant and/or solvent wherein the coating on the inner surface comprises polyvinylpyrrolidone and the outer surface of the encapsulating wall is coated with polyvinyl alcohol.

34. A composition according to claim 1 wherein the perfume is completely soluble in the surfactant and/or solvent; at least 90% by weight of the total perfume content has an octanol-water partition coefficient of greater than 2.5 (in logarithmic form to base 10) and less than 20% by weight of the total perfume content has an octanol-water partition coefficient of greater than 5 (in logarithmic form to base 10), and the diameter of the shell capsules is in the range of 1 to 10 microns; the coated shell capsules have a wall thickness in the range of 0.03 to 0.5 microns; a weight ratio of shell wall material to encapsulated material in the range of 1:10 to 1:2 and the weight ratio of solvent/surfactant:capsules in the composition is in the range of 100:1 to 5:1.

* * * * *